US00PP32908P2

(12) United States Plant Patent
van Nijnatten

(10) Patent No.: US PP32,908 P2
(45) Date of Patent: Mar. 23, 2021

(54) ***SYRINGA* PLANT NAMED 'ANNY2013-18'**

(50) Latin Name: *Syringa meyeri*
Varietal Denomination: ANNY2013-18

(71) Applicant: André van Nijnatten, Zundert (NL)

(72) Inventor: André van Nijnatten, Zundert (NL)

( * ) Notice: Subject to any disclaimer, the term of this patent is extended or adjusted under 35 U.S.C. 154(b) by 0 days.

(21) Appl. No.: 16/873,827

(22) Filed: Jul. 17, 2020

(51) Int. Cl.
*A01H 5/00* (2018.01)
*A01H 6/00* (2018.01)

(52) U.S. Cl.
USPC ..... Plt./248

(58) Field of Classification Search
USPC ..... Plt./226, 248
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Syringa* plant named 'ANNY2013-18' that is characterized by its dwarf growth habit, flowers that are large in size with panicles that are pink in color, its flowers that have a sweet fragrance, its repeat blooming in the summer and a second blooming period in autumn and its freely flowering blooming habit.

2 Drawing Sheets

Botanical classification: *Syringa meyeri.*
Variety denomination: 'ANNY2013-18'.

CROSS REFERENCE TO A RELATED APPLICATION

This application is related to U.S. Plant Patent for a plant derived from the same breeding program that is entitled *Syringa* Plant Named 'ANNY2013-02' (U.S. Plant application Ser. No. 16/873,823).

BACKGROUND OF THE INVENTION

The present invention relates to a new and distinct cultivar of *Syringa meyeri* origin that is botanically known as *Syringa* 'ANNY2013-18' and will be referred to hereafter by its cultivar name, 'ANNY2013-18'. 'ANNY2013-18' is a new cultivar of lilac grown for use as an ornamental landscape plant.

'ANNY2013-02' was discovered by the Inventor as a chance seedling in a trial plot in Zundert, The Netherlands in July of 2013. The exact parentage is unknown, however it is most likely that *Syringa* 'Pink Perfume' (U.S. Plant Pat. No. 24,252) is a probable parent based on its characteristics and its proximity to the new cultivar.

Asexual propagation of the new cultivar was first accomplished by rootstock grafting in 2015 under the direction of the Inventor in Zundert, The Netherlands. Asexual propagation by rootstock grafting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'ANNY2013-18' as a unique cultivar of *Syringa.*

1. 'ANNY2013-18' exhibits a dwarf growth habit.

2. 'ANNY2013-18' exhibits flowers that are large in size with panicles that are deep pink in color with red-purple flower buds.
3. 'ANNY2013-18' exhibits flowers that have a sweet fragrance.
4. 'ANNY2013-18' exhibits repeat blooming in the summer and a second blooming period in autumn.
5. 'ANNY2013-18' exhibits a freely flowering blooming habit.

The probable parent of 'ANNY2013-18', 'Pink Perfume' differs from 'ANNY2013-18' in having an upright and outwardly spreading habit. The new *Syringa* can be most closely compared to *Syringa* cultivars 'Palibin' (not patented), 'Superba' (not patented), and 'ANNY2013-02'. 'Palibin' and 'Superba' are both similar to 'ANNY2013-18' in having flowers that are pink in color. 'Palibin' differs from 'ANNY2013-18' in having a low spreading growth habit. 'Superba' differs from 'ANNY2013-18' in having a taller and spreading growth habit. 'ANNY2013-02' differs from 'ANNY2013-18' in having white flowers with the flower buds tinged with pink.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure include but may not be limited to a website listing by Concept Plants; the breeder's representative for licensing future propagation.

BRIEF DESCRIPTION OF THE DRAWINGS

The accompanying colored photographs illustrate the overall appearance and distinct characteristics of the new

*Syringa*. The photographs were taken of 2-year-old plants as grown outdoors in 2-liter containers at a nursery in Zundert, The Netherlands.

Figure 1:
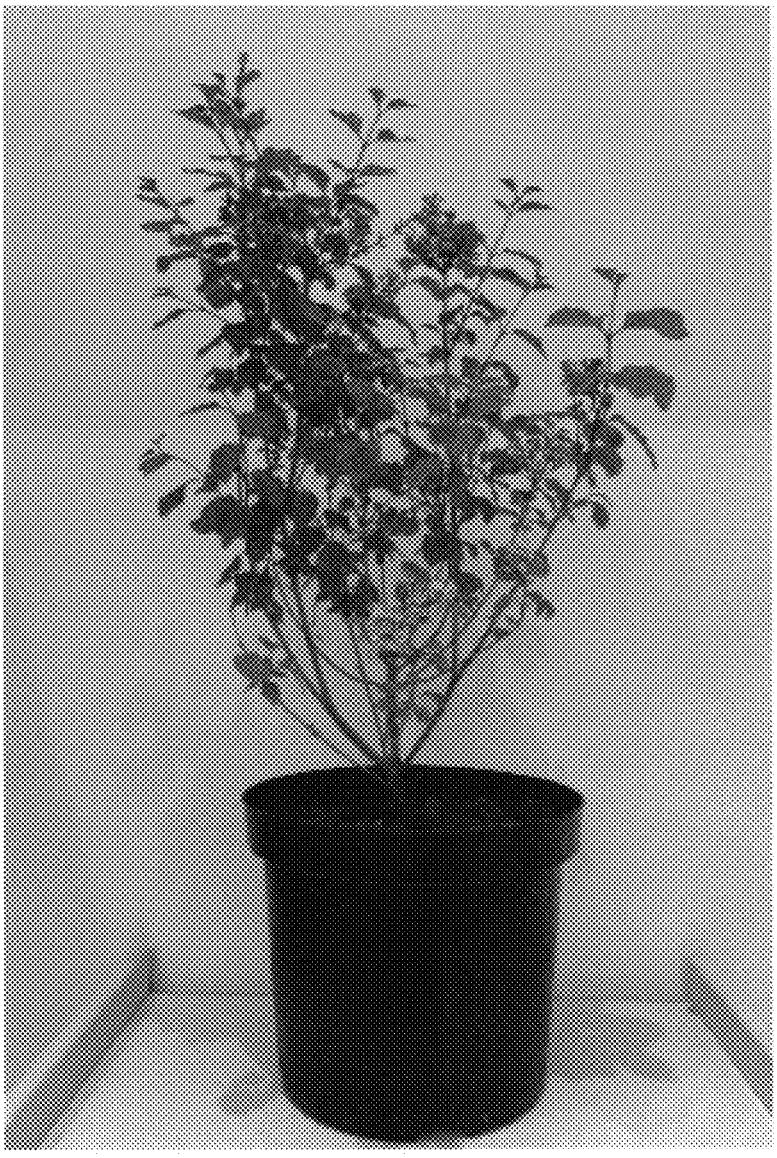

The photograph in FIG. 1 provides a side view of a plant of 'ANNY2013-18' in bloom.

Figure 2:
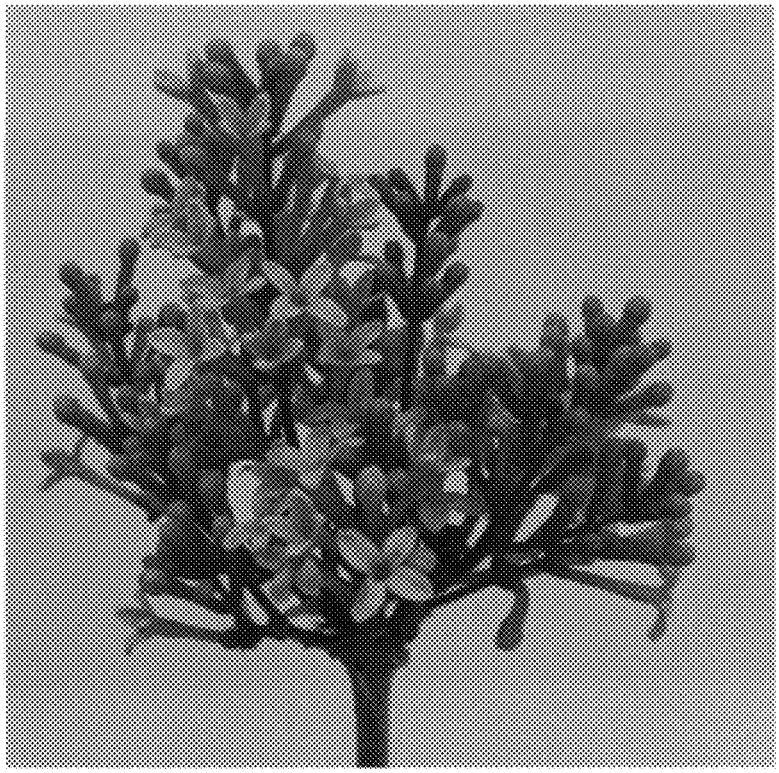

The photograph in FIG. 2 provides a close-up view of an inflorescence of 'ANNY2013-18'.

Figure 3:
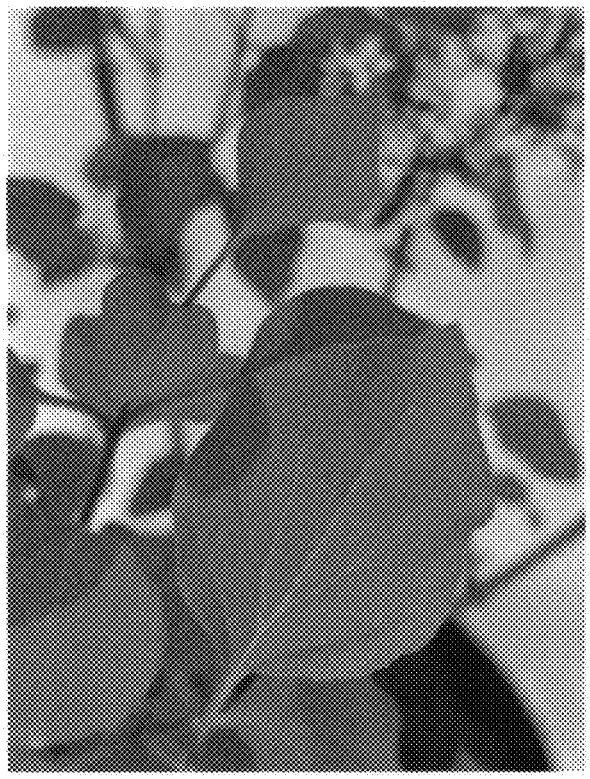

The photograph in FIG. 3 provides a close-up view of the foliage of 'ANNY2013-18'.

The colors in the photographs are as close as possible with the photographic and printing technology utilized and the color values cited in the detailed botanical description accurately describe the colors of the new *Syringa*.

DETAILED BOTANICAL DESCRIPTION

The following is a description of 2-year-old plants as grown outdoors in 2 liter containers in Zundert, The Netherlands. The phenotype of the new cultivar may vary with variations in environmental, climatic, and cultural conditions, as it has not been tested under all possible environmental conditions. The color determination is in accordance with The 2007 Colour Chart of The Royal Horticultural Society, London, England, except where general color terms of ordinary dictionary significance are used.

General description:

*Blooming period.*—Spring with reblooming in summer and again in Autumn in The Netherlands.

*Plant type.*—Deciduous shrub.

*Plant shape.*—Broadly ovate.

*Plant habit.*—Dwarf, dense and compact.

*Height and spread.*—An average of 110 cm an height and 60 cm in width as a 2-year-old plant.

*Hardiness.*—At least in U.S.D.A. Zones 5 through 9.

*Diseases and pests.*—No susceptibility or resistance to diseases or pests has been observed.

*Root description.*—Fibrous and dense, a blend of 165A and 161D in color.

*Propagation.*—Rootstock grafting.

*Growth rate.*—Moderate.

*Root development.*—Grafts root in 4 to 6 weeks in June-August, plugs are overwintered and planted in P9 containers the following spring.

Branch description:

*Branch shape.*—Rounded.

*Branch color.*—Young and mature stems N186C and 200B, older bark 148A in color.

*Branch size.*—Average of 15.1 cm in length, 2.5 mm in diameter.

*Branch surface.*—Smooth and moderately covered with soft pubescent hairs average of 0.5 mm in length, NN155C in color.

*Branch quantity.*—Average of 5 main branches, average of 6 lateral branches per main branch.

*Branch strength.*—Strong.

*Internode length.*—2.9 cm in length.

*Branching.*—Held upright to slightly outward.

Foliage description:

*Leaf shape.*—Broadly ovate to cordate.

*Leaf division.*—Simple.

*Leaf base.*—Obtuse to short attenuate.

*Leaf apex.*—Acute.

*Leaf fragrance.*—None.

*Leaf venation.*—Pinnate, upper surface 147C in color, lower surface 147D in color.

*Leaf margins.*—Entire and slightly undulate.

*Leaf arrangement.*—Opposite.

*Leaf attachment.*—Petiolate.

*Leaf surface.*—Upper and lower surface smooth and slightly leathery, lower surface is sparsely pubescent covered with short soft hairs 0.75 mm in length, NN155C in color.

*Leaf size.*—An average of 3.9 cm in length and 3 cm in width.

*Leaf quantity.*—An average of 12 (6 pairs) per mature branch.

*Leaf color.*—Young leaves upper surface; 146A, young leaves lower surface; 146B, mature leaves upper surface; 138A and 143A, mature leaves lower surface; 138B.

*Petioles.*—An average of 9 mm in length and 1 mm in width, color; upper surface 178A to 178B, lower surface 177B to 177C.

Inflorescence description:

*Inflorescence type.*—Terminal and axillary panicles.

*Inflorescence size.*—An average of 10.1 cm in height and 6.2 cm in width.

*Peduncles.*—An average of 8.9 cm in length and 1.5 mm in diameter, glabrous and slightly glossy surface, moderate strength, 197A in color, held vertical.

*Flower buds.*—Average of 50 per lateral stem, spathulate in shape, an average of 1.2 cm in length and 2.5 mm diameter, slightly glossy and glabrous surface, 70C to 70D in color, buds open approximately 5 days after stage described.

*Flower fragrance.*—Sweet, strong, lilac scent.

*Persistence of flowers.*—Self-cleaning.

*Lastingness of flowers.*—Individual panicles bloom for about 10 days.

*Flower quantity.*—An average of 100 flowers per lateral stem.

*Flower type.*—Salverform.

*Flower aspect.*—Upwards and slightly outward.

*Flower size.*—An average of 9 mm in diameter, 1.3 cm in depth.

*Petals.*—4, free petal lobes; an average of 1.5 cm in length and 2 mm in width, narrow oblanceolate in shape with acute apex, entire margins, margins of the free lobes moderately involute, lower 77% fused forming a narrow tube, color; when opening upper surface 73B to 73C, margins 73D, tube 73B to 73C, when opening lower surface; 70C, when fully open upper and lower surface 70C.

*Calyx.*—Rotate, 1.5 mm in length and diameter.

Reproductive organs:

*Pistils.*—1, average of 3 mm in length, stigma; club-shaped, NN155C in color, style; average of 2 mm in length, NN155C in color, ovary 146A in color.

*Stamens.*—2, anthers; dorsifixed, sessile (no filament) and implanted into inner side of tube, an average of 2 mm in length and N77B in color, pollen; moderate in quantity and 4B in color.

*Fruit and seed.*—No seed or fruit has been observed to date.

It is claimed:

1. A new and distinct cultivar of *Syringa* plant named 'ANNY2013-18' as herein illustrated and described.

* * * * *